US00PP36039P3

(12) United States Plant Patent
Bennett

(10) Patent No.: US PP36,039 P3
(45) Date of Patent: Jul. 30, 2024

(54) ROSE HYBRIDA SHRUB NAMED 'AUSernie'

(50) Latin Name: *Rosa hybrida*
Varietal Denomination: AUSernie

(71) Applicant: David Austin Roses Ltd., Wolverhampton (GB)

(72) Inventor: Carl Bennett, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 17/803,799

(22) Filed: Nov. 29, 2022

(65) Prior Publication Data

US 2024/0180048 P1 May 30, 2024

(51) Int. Cl.
*A01H 5/02* (2018.01)
*A01H 6/74* (2018.01)

(52) U.S. Cl.
USPC ..... Plt./104
CPC ..... *A01H 6/749* (2018.05)

(58) Field of Classification Search
USPC ..... Plt./104
CPC ..... A01H 6/749; A01H 5/02
See application file for complete search history.

*Primary Examiner* — Keith O. Robinson

(57) ABSTRACT

A variety of rose plant of the shrub class, named 'AUSernie'. The 'AUSernie' is a variety of a rose deeply filled, cupped rosettes of sunset yellow-orange, paling to apricot, and a healthy and upright, bushy shrub with a medium-strong Myrrh fragrance.

1 Drawing Sheet

Classification: The present invention relates to a new *Rosa hybrida* shrub of the market class 'English Rose'.

Variety denomination: The new plant has the varietal denomination 'AUSernie'.

ORIGIN OF INVENTION

This invention relates to a new and distinct variety of shrub rose plant named 'AUSernie', which was originated from the cross-pollination of the two 'unnamed' and unpatented seedlings of *Rosa hybrida*.

BACKGROUND OF THE INVENTION

The primary objective of this breeding was to produce a rose with deeply filled, cupped rosettes of sunset yellow-orange, paling to apricot, and a healthy and upright, bushy shrub with a medium-strong Myrrh fragrance.

SUMMARY OF THE INVENTION

Among the features which distinguish the new variety from others presently available and commercial rose cultivars known to the inventor is the following combination of characteristics: yellow-orange blooms paling to apricot, cupped rosette shaped blooms, medium strong Myrrh fragrance.

Asexual reproduction of the new variety by budding as performed in Albrighton, United Kingdom shows that the foregoing and other distinguishing characteristics come true to form and are established and transmitted through succeeding asexual propagations. 'AUSernie' may be asexually propagated by budding. The budding successfully occurred on an unpatented plant/rootstock *Rosa dumetorum* 'Laxa' for the observed plants.

COMPARISON WITH PARENTS

The maternal and paternal parents of 'AUSernie' are two unnamed seedlings. The new rose may be distinguished from its seed parent, by the following combination of characteristics: the seed parent has fewer petals and these are held in a much looser manner when compared to 'AUSernie'. The new rose may be distinguished from its pollen parent, by the following combination of characteristics: the pollen parent is more apricot/orange in color when compared to 'AUSernie', has fewer petals and, as a plant is larger overall.

COMPARISON WITH THE CLOSEST COMMERCIALLY AVAILABLE CULTIVAR

The most similar rose variety is 'AUSwinter' (U.S. Plant Pat. No. 13,484, expired November 2020). Both blooms are similar in color however 'AUSwinter' has more petals (approx. 120) when compared to 'AUSernie' (approx. 95). 'AUSwinter' also has a different growth habit, as more of a climbing rose, when compared to 'AUSernie' which is a shrub rose. There is also a difference in the number of prickles, with 'AUSwinter' having considerably more prickles than 'AUSernie'. Finally, the leaf glossiness of the upper side is weaker on 'AUSwinter' when compared to 'AUSernie'.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSernie' specimens were made at a garden in Albrighton, Wolverhampton, United Kingdom. The following description is of 6-year-old rose plants of the new variety grown in a garden environment in Albrighton, United Kingdom in the month of June. Phenotypic expression may vary with environmental, cultural and climatic conditions, as well as differences in conditions of light and soil.

FLOWER CHARACTERISTICS

Blooming habit: Recurrent. The number of blooms per plant during the growing season is profuse, but there are too many to count.

Bud:

*Size*.—About 2.9 cm long and 2.2 cm in diameter when the petals start to unfurl.

*Form*.—The bud form is long pointed ovoid.

*Color*.—When sepals first divide, the bud color is RHS 13A (yellow group) with flashes of RHS 34C (orange-red group). When half blown, the upper sides of the petals are RHS 13B (yellow group).

*Calyx*.—Shape: star shape, with the sepals folding back against the stems. Length: 6.6 cm. Diameter: 6.6 cm.

*Sepals*.—Arrangement: Regularly arranged. Color: Upper Surface: RHS 144B (yellow-green group) in center with RHS 146B (yellow-green group) on perimeter. Lower Surface: RHS 144A (yellow-green group). Length: 2.9 cm. Width: 1.15 cm. Shape: Lanceolate. Margin: Hairy. Surface texture: Upper Surface: Hairy. Lower Surface: Smooth. Number: There are 2 lightly appendaged sepals, and 3 unappendaged sepals with hairy edges.

*Receptacles*.—Color: RHS 144A (yellow-green group) with a ring of RHS 60B (red-purple group) at apex. Shape: Apple. Size: Medium, about 1 cm long×1 cm wide. Surface: Smooth.

*Peduncle*.—Length: Medium, averaging about 5.4 cm. Surface: Smooth. Color: RHS 144C (green-yellow group). Strength: Normal.

Blooms:

*Type*.—Double.

*Size*.—Large, average open diameter is about 10.1 cm and average depth is about 4 cm.

*Borne*.—Several together in clusters of 2-6 with blooms having a rounded shape.

*Penduncle*.—Strength: Normal, average length is about 5.4 cm. Diameter: 0.2 cm.

*Form*.—When first open, bloom is cupped/globular. Permanence of bloom flattens: outer petals curl back.

*Upper profile*.—Flat.

*Lower profile*.—Flattened convex.

Petalage: Number of petals under normal conditions: 95.

*Color*.—The upper sides of the petals are RHS 13C (yellow group). The reverse sides of the petals are RHS 6D (yellow group).

*Variegations*.—None.

*Discoloration*.—The general tonality at the end of the first day is RHS 15A (yellow group), and at the end of the third day is RHS 13C (yellow group).

*Fragrance*.—Moderate strong. Character of fragrance: Myrrh.

Petals:

*Texture*.—Smooth, satiny and thin on both sides.

*Size*.—Width: 2.8 cm. Length: 4.6 cm.

*Surface*.—Smooth.

*Shape*.—Obovate.

*Margin*.—Outer petals sometimes emarginate (notch at tip).

*Apex shape*.—Rounded — sometimes emarginate.

*Base shape*.—Obtuse.

*Form*.—Generally incurved — some tips slightly recurved.

*Arrangement*.—Informal.

*Basal spot*.—Not ascertainable.

*Petaloids*.—Number: 6-10. Color: RHS 10B (yellow group). Length: 1.4 cm. Width: 0.7 cm. Shape: Obovate. Margin: Uniform.

*Persistence*.—Petals hang on and dry.

*Lastingness*.—On the plant: Fair about 7 days. As a cut flower: not tested.

Reproductive parts:

*Stamens*.—Number: approximately 65-70. Length: approximately 1 cm.

*Anthers*.—Length: approximately 0.25 cm. Color: RHS 11A (yellow group). Arrangement: Regular around styles.

*Filaments*.—Color: RHS 11A (yellow group). Length: 0.8 cm.

*Pollen*.—Color: RHS 6C (yellow group). Amount: Moderate.

*Pistils*.—Number: approximately 45. Length: approximately 1.1 cm.

*Styles*.—Color: RHS 157D (green-white group). Length: 0.9 cm.

*Stigmas*.—Color: RHS 11A (yellow group) with a tinge of RHS 179A (greyed-red group). Length: approximately 0.2 cm.

*Hips*.—NONE Observed.

PLANT CHARACTERISTICS

Plant form: Shrub.

Plant growth: Medium and upright.

Age to maturity: 2 years.

Mature plant: Height: 120 cm. Width: 110 cm.

Rootstock: *Rosa dumetorum* 'Laxa' (not patented) for the observed plants in the United Kingdom. 'Dr Huey' (not patented) in the USA.

Foliage:

*Number*.—Leaflets on normal mid-stem leaves is: 5 with instances of 7 (including terminal leaflet).

*Size*.—Large/medium, about 14.5 cm long×10.3 cm wide.

*Quantity*.—Normal. Number of leaves per flowering stem is: approximately 5-7.

*Color*.—New foliage: Upper side: RHS 152B (red-purple group). Lower side: RHS 59C (red-purple group). Old foliage: Upper side: RHS 146A (yellow-green group). Lower side: RHS 146B (yellow-green group).

*Glossiness*.—Moderate.

Leaflets:

*Size*.—About 5 cm long×4 cm wide.

*Shape*.—Pointed oval.

*Base shape*.—Rounded.

*Apex shape*.—Acuminate.

*Texture*.—Upper side: Leathery. Lower side: Leathery.

*Edge*.—Serrated.

*Serrations*.—Single/Small.

*Petiole*.—Color: upper side is RHS 61B (red-purple group), and reverse side is RHS 144A (yellow-green group). Length: 4.5 cm. Width: 0.2 cm. Surface Texture: Glandular.

*Petiole rachis*.—Color: upper side RHS 61B (red-purple group), and reverse side is RHS 144A (yellow-green group). Underside: smooth with prickles. Lower Surface: smooth.

*Stipules*.—Length: 3 cm. Shape: Lateral. Descriptor glandular. Apex: Acute. Color: RHS 144B (yellow-green group).

*Auricle*.—Shape: Lanceolate. Length: 0.9 cm Width: 0.3 cm. Color: RHS 144B (yellow-green group).

*Vein color*.—RHS 146A (yellow-green group).

*Venation pattern*.—Reticulate.

Wood:

*New wood*.—Color: RHS 59A (red-purple group). Bark: Smooth.

*Old wood*.—Color: RHS 144A (yellow-green group). Bark: Smooth.

Branching habit:

*Number*.—2-3 per main stem.

*Dimensions*.—Length: 60-80 cm. Diameter: 0.7 cm.

Stems:

*Mature stem*.—Length: 100 cm. Diameter: 0.9 cm.

*Internode distance*.—approximately 7.2 cm. The above measurements are all variable, depending on growing conditions in a season.

*Stem pubescence present*.—No.

Prickles:

*Quantity*.—On main canes from base: few. Number per stem length: 3-6 per 20 cm. On laterals from main canes: few. Number per stem length: 3-6 per 20 cm.

*Form*.—Concave curved inward.

*Length*.—0.6 to 0.7 cm.

*Color when young*.—RHS 61A (red-purple group).

*Color when mature*.—RHS 199D (grey-brown group).

Small prickles:

*Quantity*.—Main stalk: Few. Number per stem length: 1-2 per 20 cm. Laterals: Few. Number per stem length: 1-2 per 20 cm.

*Color*.—When young: slightly transparent RHS 61A (red-purple group). When mature: RHS 199D (grey-brown group).

Disease resistance:

*Powdery mildew* (*podosphaera pannosa*).—Resistant.

*Downy mildew* (*peronospora species*).—Resistant.

*Blackspot* (*diplocarpon rosae*).—Resistant.

*Rust* (*phragmidium tuberculatum*).—Resistant.

Pest resistance: Not tested.

Winter hardiness: Not tested.

Growing conditions: Normal garden conditions.

What is claimed is:

1. A new and distinct variety of rose plant of the shrub class named 'AUSernie', substantially as herein shown and described.

* * * * *

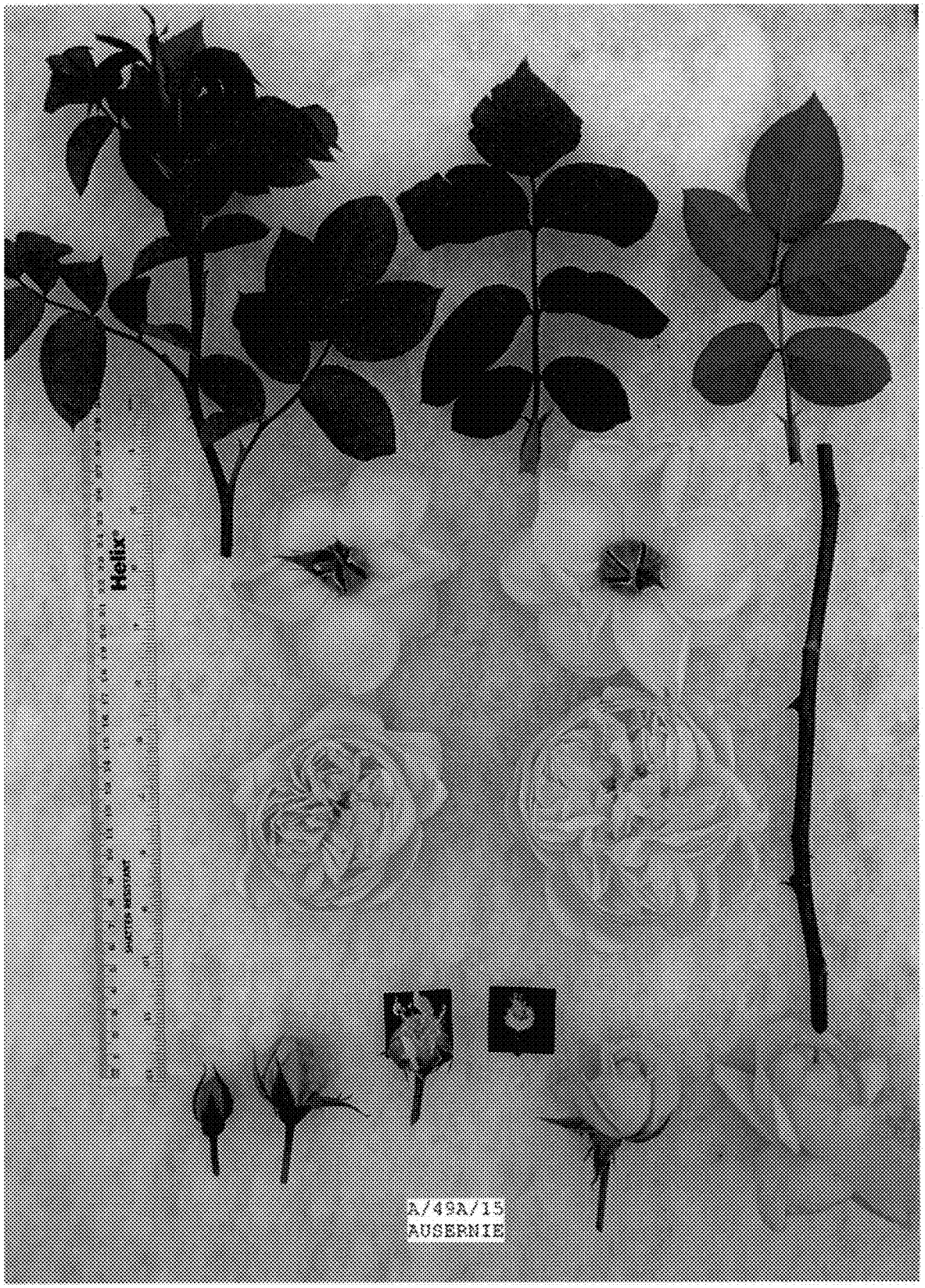
Helix
A/498/15
AUSERNIE